United States Patent
Bharadwaj et al.

(10) Patent No.: US 8,523,873 B2
(45) Date of Patent: Sep. 3, 2013

(54) NEURAL-MONITORING ENABLED SLEEVES FOR SURGICAL INSTRUMENTS

(75) Inventors: Jeetendra S. Bharadwaj, Memphis, TN (US); Bradley E. Steele, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 640 days.

(21) Appl. No.: 12/756,829

(22) Filed: Apr. 8, 2010

(65) Prior Publication Data

US 2011/0251597 A1    Oct. 13, 2011

(51) Int. Cl.
*A61B 17/17*    (2006.01)

(52) U.S. Cl.
USPC ................................. 606/96; 600/554

(58) Field of Classification Search
CPC .............. A61B 5/4893; A61B 17/17
USPC .......................... 606/96; 600/554
See application file for complete search history.

(56) References Cited

U.S. PATENT DOCUMENTS

| | | | | |
|---|---|---|---|---|
| 2,921,549 A * | 1/1960 | Schwenk | .......................... | 72/83 |
| 3,409,013 A * | 11/1968 | Berry | .................. | 606/1 |
| 4,092,753 A * | 6/1978 | Fuhrmann | ........................ | 7/158 |
| 4,314,565 A * | 2/1982 | Lee | ................ | 600/566 |
| 4,341,206 A * | 7/1982 | Perrett et al. | ...................... | 606/80 |
| 4,624,585 A * | 11/1986 | Nix et al. | ...................... | 384/296 |
| 4,668,138 A * | 5/1987 | Carter | .......................... | 409/234 |
| 4,750,878 A * | 6/1988 | Nix et al. | ...................... | 384/296 |
| 5,330,273 A * | 7/1994 | Tsai | ................. | 384/215 |
| 5,330,501 A * | 7/1994 | Tovey et al. | .................... | 606/198 |
| 5,417,684 A * | 5/1995 | Jackson et al. | ..................... | 606/1 |
| 5,513,517 A * | 5/1996 | Van Meter et al. | ........... | 73/54.28 |
| 5,749,272 A * | 5/1998 | Phan | ................. | 81/62 |
| 5,806,381 A * | 9/1998 | Lin | ................ | 81/58.4 |
| 5,885,006 A * | 3/1999 | Sheedy | ......................... | 384/192 |
| 5,888,200 A * | 3/1999 | Walen | ........................... | 606/167 |
| 6,146,325 A * | 11/2000 | Lewis et al. | ..................... | 600/16 |
| 6,162,234 A * | 12/2000 | Freedland et al. | ............ | 606/151 |
| 6,241,729 B1 * | 6/2001 | Estes et al. | .................. | 606/86 R |
| 6,292,701 B1 * | 9/2001 | Prass et al. | ..................... | 607/116 |
| 6,568,889 B2 * | 5/2003 | Rohm | ........................... | 409/233 |
| 6,602,248 B1 * | 8/2003 | Sharps et al. | ................... | 606/32 |
| 7,033,363 B2 * | 4/2006 | Powell | .............................. | 606/96 |
| 7,077,847 B2 * | 7/2006 | Pusnik et al. | .................... | 606/96 |
| 7,284,936 B1 * | 10/2007 | Rinner | .......................... | 408/240 |
| 7,303,553 B2 * | 12/2007 | Ott | ............................... | 604/533 |
| 7,387,053 B2 * | 6/2008 | Lee | ................ | 81/177.1 |
| 7,465,306 B2 * | 12/2008 | Pond et al. | .................. | 606/86 A |
| 7,544,208 B1 * | 6/2009 | Mueller et al. | ............. | 623/17.15 |
| 7,643,884 B2 * | 1/2010 | Pond et al. | .................... | 607/116 |
| 7,708,287 B2 * | 5/2010 | Fajardo | ........................ | 279/2.03 |
| 7,717,932 B2 * | 5/2010 | McFarlin et al. | .............. | 606/170 |
| 7,811,138 B2 * | 10/2010 | Santangelo et al. | ............ | 439/728 |

(Continued)

*Primary Examiner* — Sam Yao
*Assistant Examiner* — Manolis Pahakis (57) ABSTRACT

A neural monitoring enabled insulating sleeve for use with a surgical instrument during a surgical procedure on a patient in patient body tissue includes a tubular portion having a proximal end, a distal end, and a bore extending therethrough. The bore is configured to receive the surgical instrument. The tubular portion being formed of a material that electrically insulates the surgical instrument from the patient body tissue and having a flexible portion configured to flex between a locked and an unlocked condition. A camming component is configured to interface at the proximal end of the tubular portion. It is configured to cam the flexible portion between the locked and unlocked condition.

17 Claims, 8 Drawing Sheets

(56) References Cited

U.S. PATENT DOCUMENTS

| | | | |
|---|---|---|---|
| 7,824,327 B2* | 11/2010 | Smith | 600/114 |
| 7,905,875 B2* | 3/2011 | Smith et al. | 604/508 |
| 7,918,876 B2* | 4/2011 | Mueller et al. | 606/251 |
| 7,971,508 B2* | 7/2011 | Kozak | 81/53.2 |
| 8,016,846 B2* | 9/2011 | McFarlin et al. | 606/170 |
| 8,152,851 B2* | 4/2012 | Mueller et al. | 623/17.15 |
| 8,241,313 B2* | 8/2012 | McFarlin et al. | 606/170 |
| 8,277,450 B2* | 10/2012 | Dees et al. | 606/62 |
| 8,425,430 B2* | 4/2013 | Pond et al. | 600/554 |
| 8,442,621 B2* | 5/2013 | Gorek et al. | 600/424 |
| 2002/0189674 A1* | 12/2002 | Meeder | 137/359 |
| 2004/0225228 A1* | 11/2004 | Ferree | 600/554 |
| 2006/0015086 A1* | 1/2006 | Rasmussen et al. | 604/533 |
| 2006/0127158 A1* | 6/2006 | Olson et al. | 401/53 |
| 2006/0173521 A1* | 8/2006 | Pond et al. | 607/116 |
| 2006/0190001 A1* | 8/2006 | Powell | 606/96 |
| 2006/0200023 A1 | 9/2006 | Melkent et al. | |
| 2007/0016166 A1* | 1/2007 | Thistle | 604/533 |
| 2007/0203477 A1 | 8/2007 | Lechot | |
| 2007/0239187 A1* | 10/2007 | Brunnett et al. | 606/172 |
| 2009/0062807 A1* | 3/2009 | Song | 606/87 |
| 2009/0062833 A1* | 3/2009 | Song | 606/191 |
| 2009/0138050 A1* | 5/2009 | Ferree | 606/279 |
| 2009/0221153 A1* | 9/2009 | Santangelo et al. | 439/18 |
| 2010/0036384 A1* | 2/2010 | Gorek et al. | 606/104 |
| 2010/0094115 A1* | 4/2010 | Pond et al. | 600/373 |
| 2010/0198219 A1* | 8/2010 | McFarlin et al. | 606/45 |
| 2010/0312103 A1* | 12/2010 | Gorek et al. | 600/425 |
| 2011/0196205 A1* | 8/2011 | Hathaway et al. | 600/201 |
| 2011/0230965 A1* | 9/2011 | Schell et al. | 623/17.11 |
| 2012/0059480 A1* | 3/2012 | Schell et al. | 623/17.16 |
| 2012/0253361 A1* | 10/2012 | Drstvensek et al. | 606/130 |

* cited by examiner

NEURAL-MONITORING ENABLED SLEEVES FOR SURGICAL INSTRUMENTS

FIELD OF THE INVENTION

The present disclosure is directed to sleeves for surgical instruments, and more particularly, is directed to neural-monitoring enabled sleeves that cover surgical instruments such as, for example, taps, bits, drivers, reamers, and others.

BACKGROUND

Neural integrity monitoring systems use electro stimulation to identify nerve location to predict and prevent neurological injury. In order to avoid shunting into the patient's anatomy, the body portions of conventional neural integrity monitoring instruments, such as taps and screw drivers, include an electrically insulative coating. Because this insulative coating is applied to the metal instrument, it is prone to scratching and chipping, exposing the conductive metal of the instrument. For example, the coating may be damaged through common use, distribution, cleaning, and sterilization cycles. Because contact between patient tissue and any portion of the exposed metal body can compromise the effectiveness and accuracy of the neural integrity monitoring system, these instruments require careful handling to avoid inadvertent coating damage. Further, coating the bodies of the instruments increases manufacturing costs resulting in higher medical costs to the consumer.

The sleeves and instruments disclosed herein overcome one or more of the shortcomings of prior art devices.

SUMMARY

In one exemplary aspect, the present disclosure is directed to a neural-monitoring enabled insulating sleeve for use with a surgical instrument during a surgical procedure in patient body tissue. The sleeve includes a tubular portion having a proximal end, a distal end, and a bore extending therethrough. The bore is configured to receive the surgical instrument. The tubular portion is formed of a material that electrically insulates the surgical instrument from the patient body tissue and has a flexible portion configured to flex between a locked and an unlocked condition. A camming component is configured to interface at the proximal end of the tubular portion. It is configured to cam the flexible portion between the locked and unlocked condition.

In one exemplary aspect, the flexible portion is unflexed when in the unlocked condition such that the flexible portion extends in a direction along an axis of the tubular portion, and the flexible portion is flexed when in the locked condition, such that the flexible portion is angled relative to the axis of the tubular portion. In another exemplary aspect, the tubular portion comprises a first bore having a bore bottom surface and a second bore extending from the bore bottom surface to the distal end.

In another exemplary aspect, the present disclosure is directed to an assembly for use during a surgical procedure. The assembly includes a surgical instrument having a distal end, a proximal end, and cylindrical body portion extending therebetween. The body portion includes a connection feature. The assembly also includes a tubular portion having a proximal end, a distal end, and a bore extending therethrough. The bore is configured to receive the surgical instrument. The tubular portion is neural-monitoring compatible by being formed of a material that electrically insulates the surgical instrument from patient body tissue. It has a flexible portion configured to flex between a locked condition and an unlocked condition. It is arranged to interface with the connection feature formed in the body portion of the surgical instrument to lock the tubular portion to the surgical instrument. The assembly also includes a camming component disposed at the proximal end of the tubular portion. The camming component is configured to rotate relative to the tubular portion to cam the flexible portion between the locked and unlocked condition.

In one aspect, the flexible portion interfaces with the connection feature to restrict relative axial movement and the permit free rotational movement.

In yet another exemplary aspect, the present disclosure is directed to a method of assembling and operating a surgical tool. The method includes the steps of inserting a surgical instrument into a driving tool and inserting a sleeve assembly over the surgical instrument. The sleeve assembly includes a camming component and a tubular portion formed of a material insulating the surgical instrument from patient body tissue. The step of inserting includes orienting the sleeve component so that the working end of the surgical instrument protrudes out of the tubular portion. The method also includes engaging a portion of the tubular portion with the surgical instrument to secure the tubular portion to the surgical instrument. This includes rotating the camming component to displace at least a portion of the tubular portion against a connection feature on the surgical instrument.

BRIEF DESCRIPTION OF THE DRAWINGS

The accompanying drawings serve to exemplify some of the embodiments of this invention.

DETAILED DESCRIPTION

The present disclosure relates generally to the field of orthopedic surgery, and more particularly to instruments and methods for conducting surgical procedures using neural integrity monitoring systems. For the purposes of promoting an understanding of the principles of the invention, reference will now be made to embodiments or examples illustrated in the drawings, and specific language will be used to describe these examples. It will nevertheless be understood that no limitation of the scope of the invention is thereby intended. Any alteration and further modifications in the described embodiments, and any further applications of the principles of the invention as described herein are contemplated as would normally occur to one skilled in the art to which the disclosure relates.

This disclosure is directed to surgical instrument assemblies enabling neural-monitoring during surgeries, such as spinal surgeries, for example. The surgical instrument assemblies include a neural-monitoring enabling sleeve assembly that can slide over a surgical instrument, like a tap, drill bit, screw driver, reamer, or other instrument. This sleeve assembly provides an electrically insulating cover over the surgical instruments so that the neural-monitoring electrical current to the surgical instrument is less likely to unintentionally shunt into the patient's anatomy, thereby increasing the accuracy in the readings obtained by the neural-monitoring equipment.

In addition, the sleeve assembly uses a locking arrangement that simply secures it in place on the surgical instrument. The locking arrangement allows the sleeve to freely rotate about the surgical instrument, allowing the surgeon to hold the sleeve for support or leverage while the instrument is rotating. This can increase the efficiency of the surgery and provide the surgeon with additional leverage and confidence during the procedure. In addition, because the sleeve assembly freely rotates relative to the surgical instrument, tissue adjacent the sleeve assembly is less likely to become wrapped around or further damaged because the sleeve need not rotate with the instrument. Accordingly, the tissue may be better protected from the rotating surgical instrument. In some embodiments, the sleeve assembly is manufactured of materials having mechanical and chemical properties that allow it to withstand common use, distribution, cleaning, and sterilization cycles. Therefore, some embodiments may be reusable.

Figure 1:
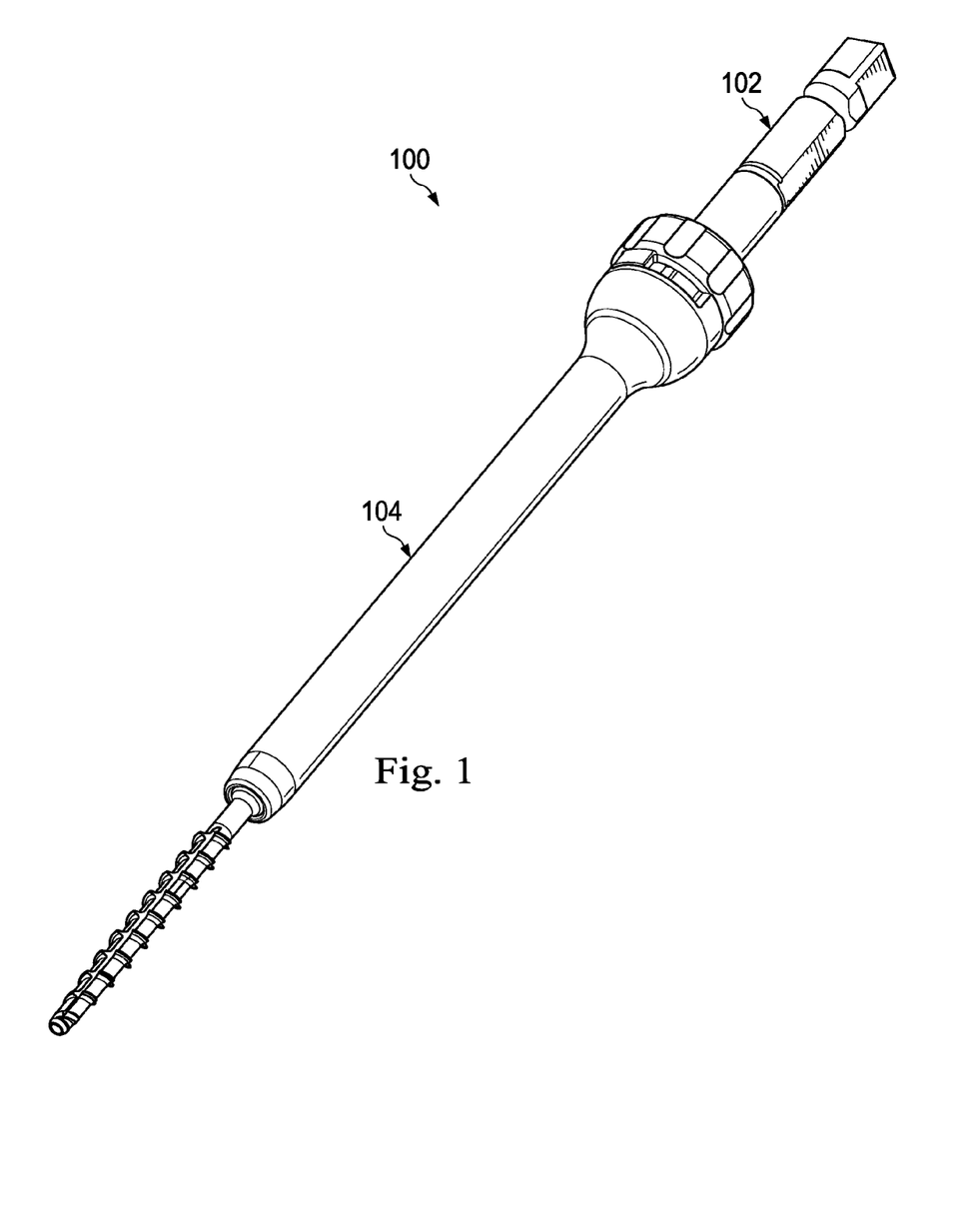
FIG. 1 is an illustration of an exemplary surgical instrument assembly including a neural-monitoring enabled sleeve assembly in the locked condition.
Figure 2:
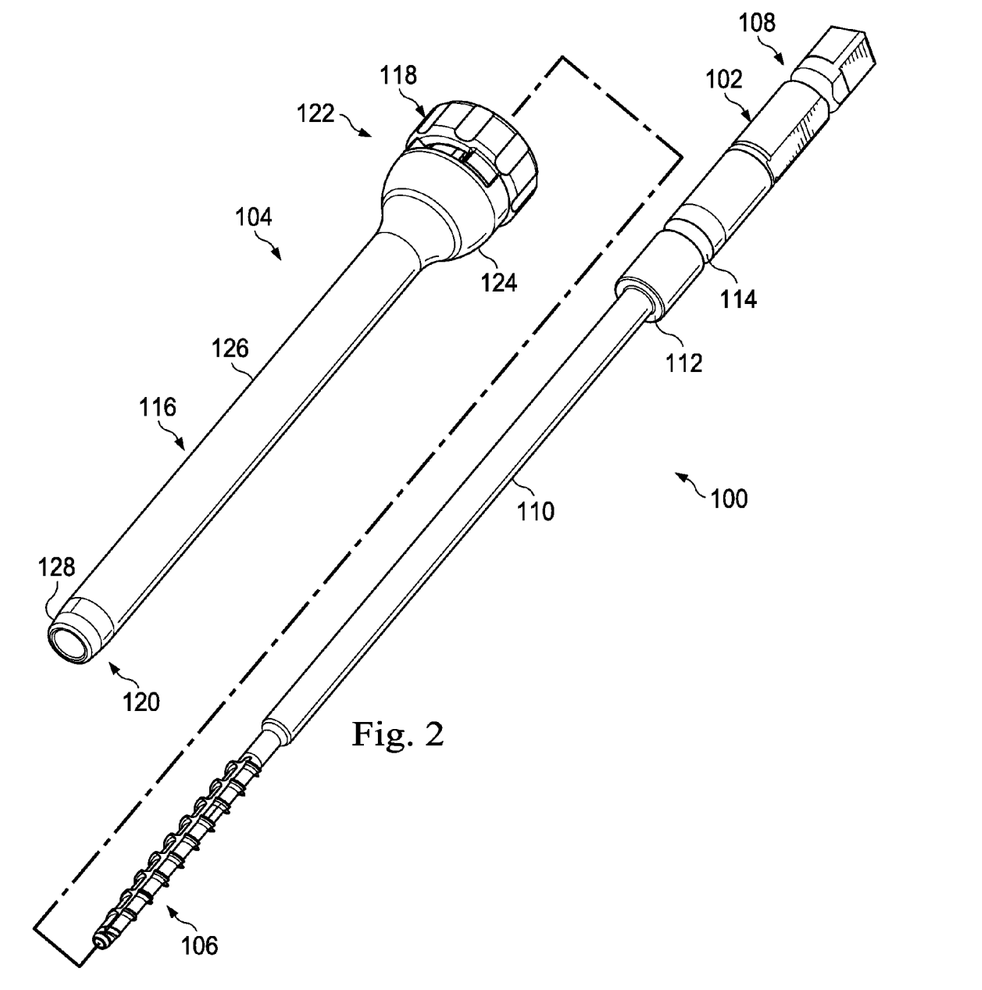
FIG. 2 is an illustration of the surgical instrument assembly of FIG. 1 in an exploded form showing the surgical instrument and the neural-monitoring enabled sleeve assembly.

FIGS. 1 and 2 show an exemplary surgical instrument assembly that may be used during a neural-integrity monitoring procedure, referenced herein by the numeral 100. In this embodiment, the surgical instrument assembly 100 includes a surgical instrument 102 and a neural-monitoring enabled sleeve assembly 104. FIG. 1 shows the assembly 100 in an assembled form ready for use, and FIG. 2 shows the assembly in a partially exploded form with the surgical instrument 102 separate from the sleeve assembly 104.

The surgical instrument 102 includes a working end 106 and a driving or proximal end 108. In the example shown, the surgical instrument 102 is a bone tap arranged to be driven by a driving tool, such as a pneumatic or electric driving tool, although it could also be manually driven. Accordingly, in this embodiment the working end 106 includes the tap thread and the proximal end 108 includes a driver interface receivable, for example, into a tool chuck (not shown). The instrument 102 includes a longitudinally extending body 110 between the working and proximal ends 106, 108. The body 110 includes a shoulder stop 112 and at least one connection feature 114, formed as a radial groove in the example in FIG. 2. Alternatively, the connection feature 114 may be formed of a radial shoulder, a protruding edge, a change in cross-sectional shape, or other feature. As will become apparent below, the distance separating the shoulder 112 and the connection feature 114 may be selected to particularly mate the surgical instrument 102 with the sleeve assembly 104.

In the embodiment shown, the surgical instrument 102 is compatible with neurological monitoring equipment. Therefore, the instrument 102 is conductive such that an electrical current applied to the surgical instrument at the proximal end 108 may be introduced to tissue being treated by the instrument's working end 106. In addition, although shown as a surgical tap, the surgical instrument may be any surgical instrument, including a drill bit, a driver for driving a screw, a reamer, or other instrument, for example. It is contemplated that the systems disclosed herein may be used with additional types of surgical instruments.

The sleeve assembly 104 is formed to extend along and cover at least a part of the surgical instrument body 110 and, in some embodiments, at least a part of the tool forming the working end 106. FIG. 1 illustrates the sleeve assembly 104 on the surgical instrument 102.

The sleeve assembly 104 includes a tubular portion 116 and a camming collar 118. The tubular portion 116 includes a distal end 120, a proximal end 122 having a head portion 124, and a body 126 extending therebetween. In this embodiment, the tubular portion 116 includes a cylindrical bore 117 (shown in cross-section in FIG. 5A) extending from the distal end 120 to the proximal end 122. The cylindrical bore 117 is sized to receive the surgical instrument 102.

The tubular portion's distal end 120 is formed with a tapered outer surface 128. This eases insertion of the sleeve assembly through patient tissue when the sleeve assembly is used during percutaneous procedures. This, therefore, helps the sleeve assembly more easily operate in minimally invasive procedures. The tubular portion 116 also generally protects the instrument body 110 from coming into contact with patient tissue, resulting in increased accuracy and reliability of the neurological monitoring system. In conjunction with this, the tubular portion 116 is formed of an insulative or non-conductive material. Examples of suitable materials include, but are not limited to, reinforced or non-reinforced polymers, carbon-reinforced polymer composites, polymers from the Polyaryletherketone (PAEK) family, including polyetheretherketone (PEEK), carbon-reinforced PEEK, polyetherketoneketone (PEKK) and PAEK composites; polysulfone; polyetherimide; polyimide; ultra-high molecular weight polyethylene (UHMWPE); and/or cross-linked UHMWPE. Ceramic materials such as aluminum oxide or alumina, zirconium oxide or zirconia, compact of particulate diamond, and/or pyrolytic carbon may also be suitable. In one embodiment, the tubular portion 116 is formed of a polysulfone plastic, such as for example, RADEL® R polyphenylsulfone.

Figure 3:
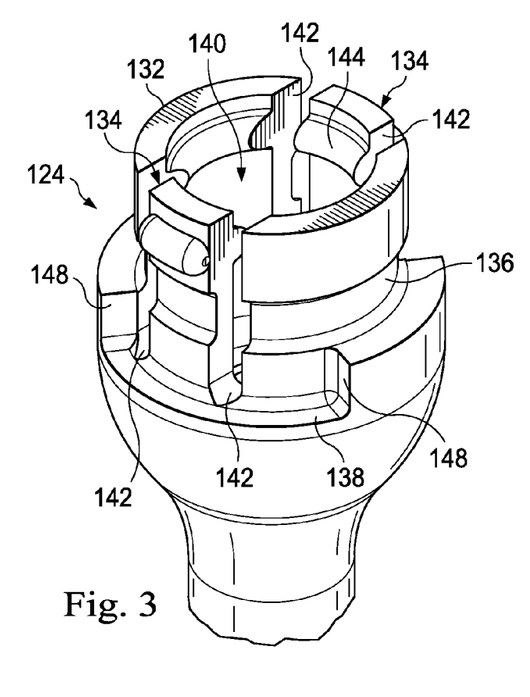
FIG. 3 is an illustration of a proximal end of a tubular portion of the neural-monitoring enabled sleeve assembly.
Figure 5A:
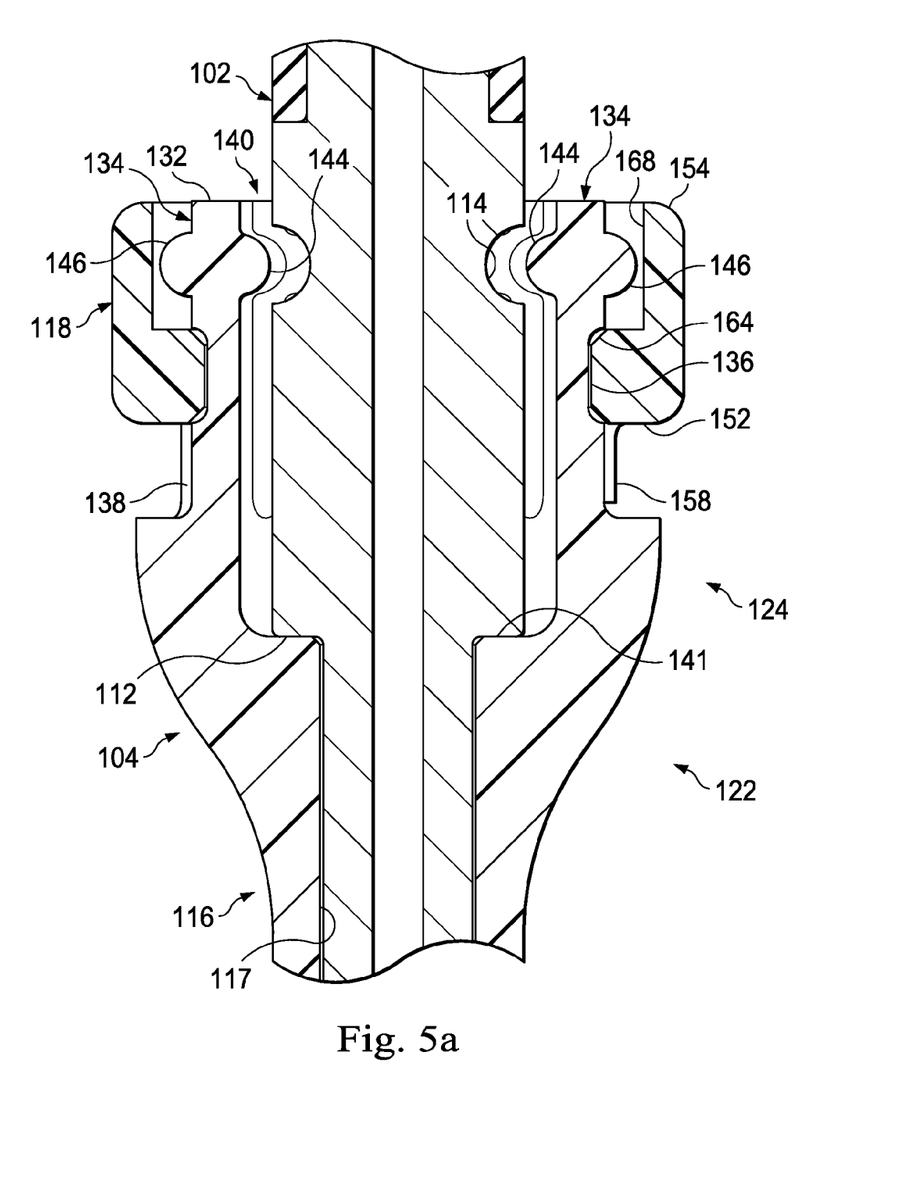
FIG. 5A is an illustration of a cross-sectional view of the proximal end of the surgical instrument assembly of FIG. 1 in an unlocked condition.

FIG. 3 illustrates the head portion 124 at the tubular portion's proximal end 122. FIG. 5A illustrates the head portion 124 in cross-section with the camming collar 118 and the surgical instrument 102. Referring to FIGS. 3 and 5A, the head portion 124 includes a portion of a locking arrangement that cooperates with the camming collar 118 to secure the sleeve assembly 104 to the surgical instrument 102.

The head portion 124 includes a proximal end surface 132, flexible fingers 134, a collar groove 136, a rotation limiting guide 138, and a central hollow bore 140. In this embodiment, the proximal end surface 132 is a flat surface forming the proximal-most end of the tubular portion 116, and extends about the opening of the bore 140. The bore 140 in the exemplary embodiment of FIG. 5A has a diameter greater than the diameter of the bore 117. A bore bottom 141 acts as an assembly stop surface that helps align the connection feature 114 of the surgical instrument 102 with the sleeve assembly 104.

The flexible fingers 134 are formed by longitudinal slots 142 extending in the axial direction in a sidewall of the head portion 124. These fingers 134 flex by elastic deformation from an unflexed condition to a flexed condition when under load. When loading is removed, the fingers 134 substantially return to their original condition. The embodiment shown includes two flexible fingers 134. It is contemplated that more or fewer flexible fingers may be used. Each has an inwardly protruding locking bearing 144 and an outwardly protruding cam interface nub 146. As will be explained further below, the locking bearing 144 attaches the sleeve assembly 104 to the surgical instrument 102, but also permits the sleeve assembly 104 to freely rotate relative to the surgical instrument 102. As shown, the locking bearings 144 and the cam interface nubs 146 are disposed substantially at the end of the flexible fingers 134, adjacent the proximal end surface 132.

The collar groove 136 extends radially about the head portion 124 and is configured to engage the camming collar 118. As will become apparent further below, the camming collar 118 connects with and rotates about the head portion 124 to create a locking arrangement that locks and unlocks the sleeve assembly 104 with the surgical instrument 102. The rotation limiting guide 138 cooperates with the camming collar 118 to limit the collar's range of rotation about the head portion 124. As such, it includes two rotation stops 148 that form the ends of the guide 138. Here, the rotation limiting guide 138 extends about 90 degrees about the head portion 124, thereby limiting the rotation range to less than 90 degrees. Other ranges, both larger and smaller, are contemplated. In the embodiment shown, the opposing side of the head portion 124 substantially minors the side shown in FIG. 3, although other arrangements are contemplated.

Figure 4:
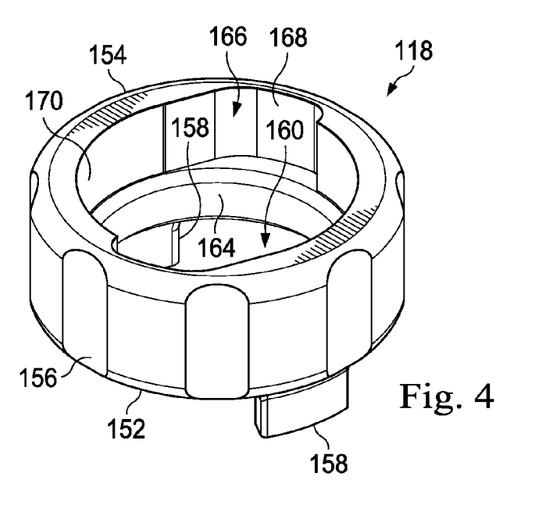
FIG. 4 is an illustration of a camming collar of the neural-monitoring enabled sleeve assembly.

Returning now to FIG. 2, the camming collar 118 fits about the proximal end 122 of the tubular portion 116, and together with the head portion 124, forms a locking arrangement that locks and unlocks the sleeve assembly 104 to the surgical instrument 102. FIGS. 4 and 5A show the camming collar 118 in greater detail.

The camming collar 118 includes a distal end 152, a proximal end 154, an outer gripping surface 156, rotation limiters 158, and an inner bore 160. When assembled the proximal end 154 lies substantially flush with the proximal end surface 132 of the tubular portion 116. The rotation limiters 158 extend distally from the distal end 152 and are arranged to fit within the rotation limiting guide 138 on the head portion 124 (FIG. 3). When the camming collar 118 is rotated relative to the head portion 124, the rotation range is mechanically limited by interference between the rotation limiters 158 and the rotation stops 148 forming ends of the rotation limiting guide 138.

The inner bore 160 is formed of a cylindrical portion 164 and a camming portion 166. The cylindrical portion 164 fits within the collar groove 136 in the head portion 124. This interface holds the camming collar 118 onto the tubular portion 116, but also allows the camming collar 118 to rotate within the groove 136 about the head portion 124. The camming portion 166 of the inner bore 160 is formed with a first diameter camming surface 168 and a different second diameter camming surface 170. The camming portion 166 is arranged to interface with the cam interface nubs 146 in the head portion 124.

Figure 5B:
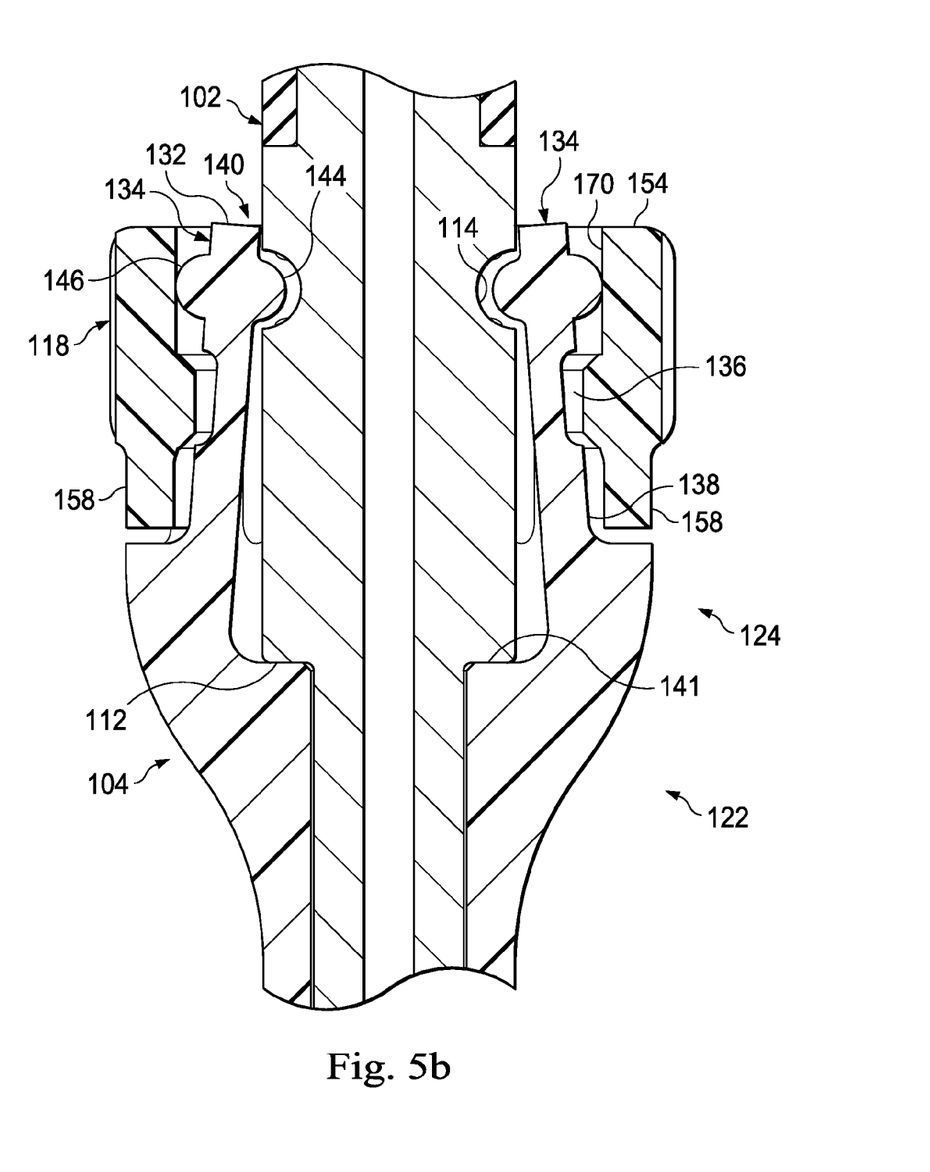
FIG. 5B is an illustration of a cross-sectional view of the proximal end of the surgical instrument assembly of FIG. 1 in a locked condition.
Figure 6A:
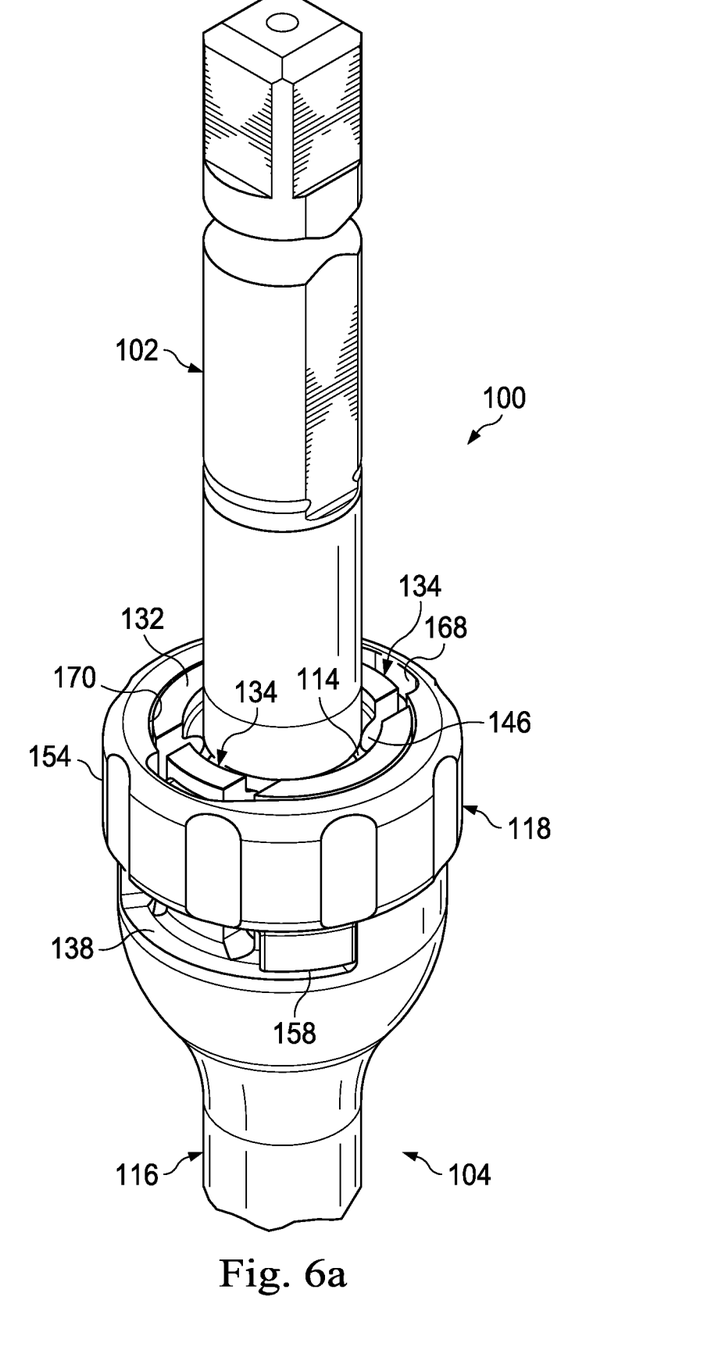
FIG. 6A is an illustration of an isometric view of the proximal end of the surgical instrument assembly of FIG. 1 in an unlocked condition.
Figure 6B:
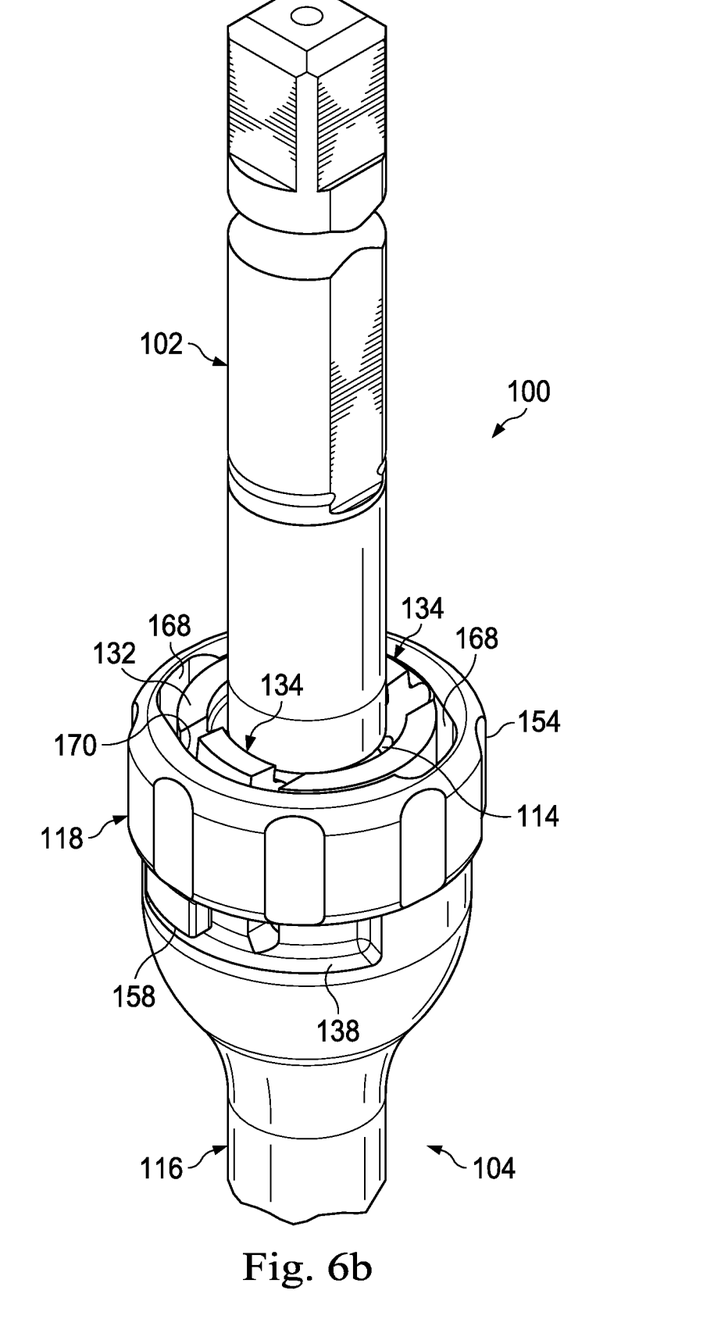
FIG. 6B is an illustration of an isometric view of the proximal end of the surgical instrument assembly of FIG. 1 in a locked condition.

The sleeve assembly 104 locks with the surgical instrument 102 when the camming collar 118 displaces the fingers 134 on the tubular portion 116 so that the locking bearings 144 on the tubular portion 116 engage with or are received in the connection feature 114 on the surgical instrument 102. FIGS. 5A and 5B illustrate the surgical instrument assembly 100 in both the locked and unlocked conditions. Particularly, FIG. 5A illustrates the unlocked condition, and FIG. 5B illustrates the locked condition. FIGS. 6A and 6B also show the unlocked and locked conditions respectively in an isometric view. When in the unlocked condition, the sleeve assembly 104 is freely axially movable along the surgical instrument 102. When in the locked condition, the sleeve assembly 104 is secured against axial movement, but freely rotates about the surgical instrument 102.

With reference to FIGS. 5A, 5B, 6A, and 6B, operation of the sleeve assembly 104 and the surgical instrument 102 will be described. Operating the surgical instrument assembly 100 includes inserting the working end 106 of the surgical instrument into the proximal end 122 of the sleeve assembly 104 and axially sliding the sleeve assembly 104 along the surgical instrument 102. As best shown in the cross-sectional views of FIGS. 5A and 5B, the sleeve assembly 104 is axially slid along the surgical instrument 102 until the surgical instrument shoulder stop 112 abuts the bore bottom surface 141 in the head portion 124. Because the distance between the shoulder stop 112 and the connection feature 114 on the surgical instrument 102 is substantially the same as the distance between the bore bottom surface 141 and the locking bearings 144 on the sleeve assembly 104, the connection feature 114 substantially aligns with the locking bearings 144. As shown in FIG. 1, in this position, the sleeve assembly 102 covers all or at least a part of the body 110 of the surgical instrument 102, thereby protecting it from inadvertent shunting due to tissue contact during a neural-monitoring procedure. It is worth noting that in some embodiments, the sleeve assembly 104 may partially cover the working end of the surgical instrument 102, or alternatively, may be shorter than that shown, thereby exposing at least a portion of the body 110.

With the shoulder stop 112 abutting the bore bottom surface 141 in the head portion 124, the surgical instrument 102 and the sleeve assembly 104 can be locked together. This is done by rotating the camming collar 118 relative to the tubular portion 116 from the unlocked condition shown in FIGS. 5A and 6A to the locked condition in FIGS. 5B and 6B.

In the unlocked condition in FIGS. 5A and 6A, the fingers 134 are aligned with the first diameter camming surfaces 168, forming a relatively larger diameter. The cam interface nubs 146 on the fingers 134 extend into cutouts that form the cam. Accordingly, in this condition, the fingers 134 are in an unbiased or unflexed state, which in the embodiment shown, means that the fingers extend in a direction substantially parallel to each other and extend substantially in the axial direction. Also in this condition, the rotation limiters 158 on the camming collar 118 are disposed substantially at one end of the rotation limiting guide 138.

Rotating the camming collar 118 relative to the tubular portion 116 causes the first and second camming surfaces 168, 170 to rotate relative to the fingers 134. At the same time, the rotation limiters 158 on the camming collar 118 move along the rotation limiting guide 138, from one side to the other. As the camming collar 118 continues to rotate, the camming surfaces 168, 170 engage and mechanically apply loading on the cam interface nubs 146, thereby flexing the fingers 134 inwardly toward the surgical instrument 102. Rotation continues until the rotation limiters 158 on the camming collar 118 abut against the rotation stop 148 at the other end of the rotation limiting guide 138. This physically limits the rotation range of the camming collar 118. In this embodiment, the cam surfaces 168, 170 and the rotation limiting guide 138 are arranged to provide camming in less than a quarter turn. Accordingly, with less than a quarter turn, or by rotating the camming collar 118 less than 90 degrees, the camming collar 118 and tubular portion 116 move from the unlocked condition to the locked condition.

In the locked condition in FIGS. 5B and 6B, the fingers 134 are aligned with the second diameter camming surface 170, forming a relatively smaller second diameter. In the locked condition, the camming surface 170 of the camming collar 118 presses against the cam interface nubs 146, biasing or flexing the fingers 134 inwardly so that the locking bearings 144 are positioned to mechanically interfere with the connection feature 114 during axial displacement. In the embodiment shown, the locking bearings 144 are the most-inward component of the head portion 124. As can be seen in FIG. 5B, the locking bearings 144 are sized and located to provide a clearance or a gap between the locking bearings 144 and the connection feature 114. Accordingly, although secured against axial movement, the locking bearings 144 rotate relatively freely within the connection feature 114, thereby allowing the sleeve assembly 104 to rotate relatively freely about surgical instrument 102.

Removal of the sleeve assembly 104 from the surgical instrument 102 is accomplished by rotating the camming collar 118 to the unlocked condition. This allows the fingers 134 to elastically return to their unlocked condition, where they disengage the connection feature 114. The sleeve assembly 104 is then disengaged from the surgical instrument 102 and the sleeve assembly 104 may be axially removed.

Figure 7:
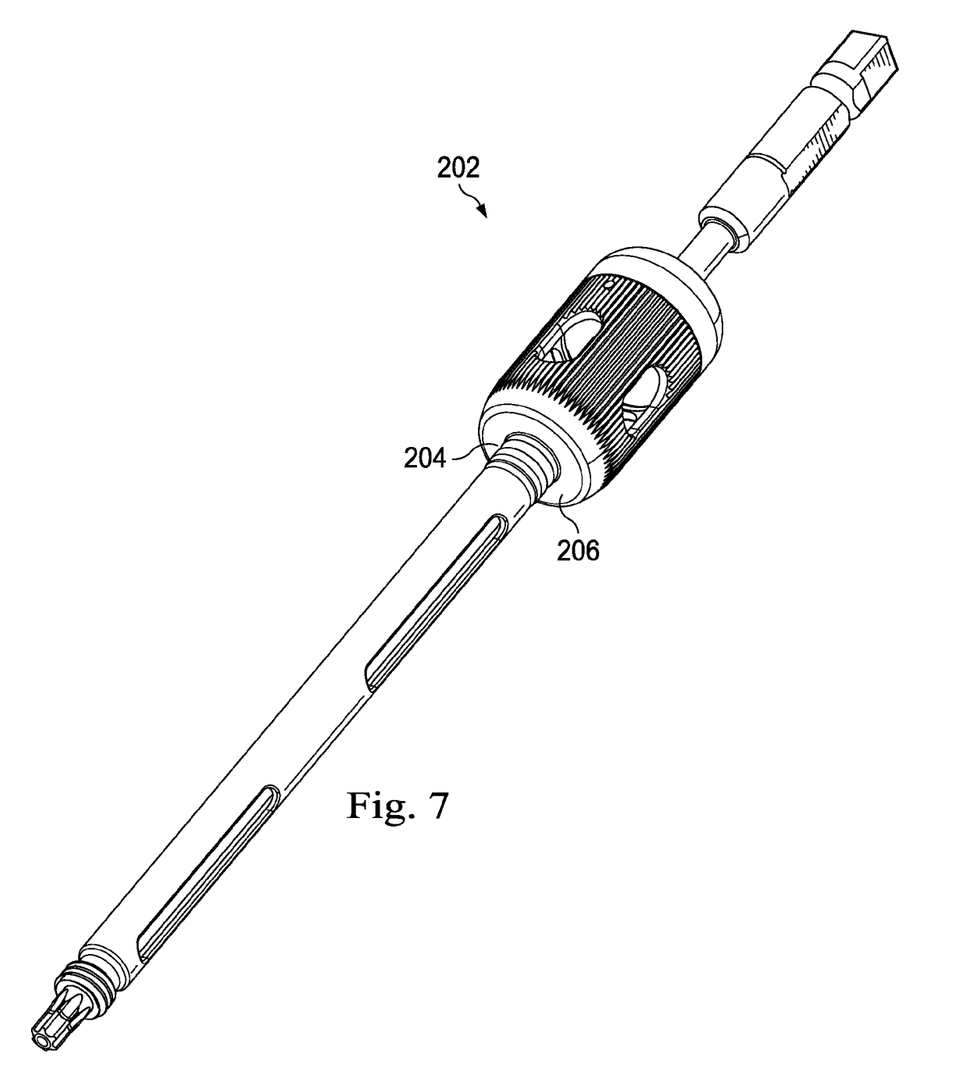
FIG. 7 is an illustration of alternative exemplary surgical instrument usable with the neural-monitoring enabled sleeve assembly.

FIG. 7 shows an alternative surgical instrument 202 usable with the sleeve assembly 104. This surgical instrument 202 is a driver for driving an implant, such as a pedicle screw, into bony tissue. Like the surgical instrument 102 described above, the surgical instrument 202 includes a connection feature 204 and a shoulder stop 206. The connection feature 204 here is shown as a radial groove or cutout. However, in this example, the shoulder stop 206 is disposed proximal of the connection feature 204, instead of distally, as shown in the surgical instrument 102 in FIG. 2. In this embodiment, when assembled with the sleeve assembly 104 described above, the connection feature 204 and the shoulder stop 206 are spaced so that when the proximal end surface 132 of the tubular portion 116 abuts against the shoulder stop 206, the locking bearings 144 on the tubular portion 116 are aligned with the connection feature 204. Accordingly, the distance between the connection feature 204 and the shoulder stop 206 on the surgical instrument 202 is substantially the same as the distance between the proximal end surface 132 and the locking bearings 144 on the sleeve assembly 104.

In use, a health care provider assembles the sleeve assembly 104 to a surgical instrument as described above. Either before or after the sleeve assembly and surgical instrument are joined, the surgical instrument may be attached to a driving tool, such as a manual, electrical, or pneumatic tool for driving the surgical instrument. The surgical instruments may be particularly suited for treating bone tissue, and in particular, for treating vertebral bone tissue, such as a pedicle. While forming a hole or otherwise treating the bone tissue, such as pedicle on a vertebra, with the surgical instrument, the health care provider may grasp the tubular portion of the sleeve assembly during drilling or tapping because it rotates freely about the surgical instrument. Therefore, although the surgical instrument may rotate, the tubular portion of the sleeve assembly connected to the surgical instrument may be held stationary. This reduces the chance of snagging and tearing gloves worn by the health care provider. Further, it may protect patient tissue from undue trauma that may occur if the tubular portion of the sleeve assembly were fixed in a manner to rotate with the surgical instrument in all circumstances.

Because the sleeve assembly 104 connects with the surgical instrument, instead of connecting with the power tool driving the surgical instrument, the sleeve assembly 104 may rotate with the surgical instrument in the absence of any force that restricts rotation of the sleeve, due to friction between the sleeve assembly and the surgical instrument. However, the forces necessary to result in rotational differences between the surgical instrument and the sleeve assembly are minimal, and are configured to be only those forces necessary to overcome the frictional surfaces between the instrument and sleeve. In some embodiments, the force to overcome the frictional forces is small enough to simply be frictional forces applied by patient tissue against the sleeve member. It is contemplated that the sleeve assembly may, in some uses, be reusable, potentially reducing the surgical costs. In other uses, the sleeve assembly is a single use device or disposable. Therefore, some embodiments may be reusable while other embodiments are disposable.

While the present invention has been illustrated by the above description of embodiments, and while the embodiments have been described in some detail, it is not the intention of the applicant to restrict or in any way limit the scope of the invention to such detail. Additional advantages and modifications will readily appear to those skilled in the art. Therefore, the invention in its broader aspects is not limited to the specific details, representative apparatus and methods, and illustrative examples shown and described. Accordingly, departures may be made from such details without departing from the spirit or scope of the applicant's general or inventive concept.

We claim:

1. A neural monitoring enabled insulating sleeve for use with a surgical instrument during a surgical procedure in patient body tissue, the sleeve comprising:
   a tubular portion that has a proximal end, a distal end, and a bore extending therethrough, the bore is configured to receive the surgical instrument, the tubular portion is formed of a material that electrically insulates the surgical instrument from the patient body tissue, the tubular portion has a head portion disposed at the proximal end, the head portion includes flexible fingers configured to flex between a locked condition such that a compressive force is applied by the flexible fingers to the surgical instrument, and an unlocked condition such that the surgical instrument is released from the flexible fingers, the tubular portion configured to freely rotate about the surgical instrument in the locked condition;
   an outwardly protruding nub disposed on each of the flexible fingers; and
   a camming collar which has an inner interface configured to engage the flexible fingers of the proximal end of the tubular portion, the inner interface is configured to cam the flexible fingers between the locked and the unlocked condition by a rotational motion of the camming collar relative to the tubular portion and includes a first camming surface and a second camming surface, the first camming surface has a larger diameter than and is recessed relative to the second camming surface, wherein the outwardly protruding nub is aligned with the first camming surface in the unlocked condition and the outwardly protruding nub is aligned and engaged with the second camming surface in the locked condition.

2. The insulating sleeve of claim 1, wherein the flexible fingers are unflexed when in the unlocked condition such that the flexible fingers extended in a direction along an axis of the tubular portion, and wherein the flexible fingers are flexed when in the locked condition, such that the flexible fingers are angled relative to the axis of the tubular portion.

3. The insulating sleeve of claim 1, wherein the tubular portion comprises a second bore extending from a distal end of the bore.

4. The insulating sleeve of claim 1, wherein the distal end of the tubular portion comprises a tapering outer surface.

5. The insulating sleeve of claim 1, wherein the flexible fingers comprise locking bearings extending radially inwardly, the locking bearings being the most-inward component of the head portion of the sleeve.

6. The insulating sleeve of claim 1, wherein the camming collar has a grippable outer surface extending about the surgical instrument.

7. An assembly for use during a surgical procedure, comprising:
   a surgical instrument having a distal end, a proximal end, and a cylindrical body portion extending therebetween, the body portion including a connection feature;
   a tubular portion that has a proximal end, a distal end, and a bore extending therethrough, the bore is configured to receive the surgical instrument, the tubular portion is formed of a neural-monitoring compatible material that electrically insulates the surgical instrument from the patient body tissue, the tubular portion has a head portion disposed at the proximal end, the head portion includes flexible fingers configured to flex between a locked condition such that a compressive force is applied by the flexible fingers to the connection feature formed in the body portion of the surgical instrument to lock the tubular portion to the surgical instrument, and an unlocked condition such that the surgical instrument is released from the flexible fingers, the tubular portion configured to freely rotate about the surgical instrument in the locked condition;
   an outwardly protruding nub disposed on each of the flexible fingers; and
   a camming collar which has an inner interface configured to engage the flexible fingers of the proximal end of the tubular portion, the inner interface is configured to cam the flexible fingers between the locked and the unlocked condition by a rotational motion of the camming collar relative to the tubular portion and includes a first camming surface and a second camming surface, the first camming surface has a larger diameter than and is recessed relative to the second camming surface, wherein the outwardly protruding nub is aligned with the first camming surface in the unlocked condition and the outwardly protruding nub is aligned and engaged with the second camming surface in the locked condition.

8. The assembly of claim 7, wherein the flexible fingers interface with the connection feature and restrict relative axial movement and permit free rotational movement.

9. The assembly of claim 7, wherein the flexible fingers comprise locking bearings extending radially inwardly.

10. The assembly of claim 9, wherein the surgical instrument comprises at least one shoulder formed thereon; and
    wherein the tubular portion includes a surface configured to abut the shoulder of the surgical instrument, the distance between the shoulder and the connection feature being the same as the distance between the surface and the locking bearings.

11. The assembly of claim 7, wherein the flexible fingers comprise locking bearings extending radially inwardly, the locking bearings engaging the connection feature in the surgical instrument to secure the tubular portion to the surgical instrument.

12. The assembly of claim 7, wherein the flexible fingers are unflexed when in the unlocked condition such that the flexible fingers extend in a direction along an axis of the tubular portion, and wherein the flexible fingers are flexed when in the locked condition, such that the flexible fingers are angled relative to the axis of the tubular portion.

13. The assembly of claim 7, wherein the distal end of the tubular portion comprises a tapering outer surface.

14. A method of assembling and operating a surgical tool comprising:
    inserting the surgical instrument of claim 7 into a driving tool;
    inserting the sleeve of claim 7 over the surgical instrument, wherein inserting includes orienting the tubular portion so that a working end of the surgical instrument protrudes out of the tubular portion;
    engaging a portion of the tubular portion with the surgical instrument to secure the tubular portion to the surgical instrument, wherein engaging comprises: rotating the camming collar to displace the flexible fingers of the tubular portion against the connection feature on the surgical instrument.

15. The method of claim 14, comprising grasping the tubular portion while simultaneously operating the driving tool to rotate the surgical instrument.

16. The method of claim 14, wherein inserting a sleeve assembly comprises sliding the sleeve assembly over the surgical instrument until a surface on the sleeve assembly abuts against a shoulder on the surgical instrument.

17. The method of claim 14, wherein rotating the camming collar to displace the flexible fingers of the tubular portion against the connection feature on the surgical instrument comprises rotating the camming collar less than 90 degrees.

* * * * *